(12) United States Patent
Bradley

(10) Patent No.: US 9,333,362 B2
(45) Date of Patent: May 10, 2016

(54) APPARATUS AND METHODS FOR STIMULATING TISSUE

(71) Applicant: BOSTON SCIENTIFIC NEUROMODULATION CORPORATION, Valencia, CA (US)

(72) Inventor: Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/486,759

(22) Filed: Sep. 15, 2014

(65) Prior Publication Data

US 2015/0005851 A1  Jan. 1, 2015

Related U.S. Application Data

(63) Continuation of application No. 12/173,169, filed on Jul. 15, 2008, now abandoned, which is a continuation of application No. 11/300,963, filed on Dec. 15, 2005, now abandoned.

(51) Int. Cl.
*A61N 1/18* (2006.01)
*A61N 1/36* (2006.01)
*A61N 1/05* (2006.01)

(52) U.S. Cl.
CPC .......... *A61N 1/36185* (2013.01); *A61N 1/0529* (2013.01); *A61N 1/0551* (2013.01); *A61N 1/36071* (2013.01); *A61N 1/0553* (2013.01)

(58) Field of Classification Search
CPC .......... A61N 1/36053; A61N 1/36057; A61N 1/3606; A61N 1/36071; A61N 1/36185
USPC ................................ 607/2, 46, 117
See application file for complete search history.

(56) References Cited

U.S. PATENT DOCUMENTS

| | | |
|---|---|---|
| 3,738,368 A | 6/1973 | Avery et al. |
| 3,774,618 A | 11/1973 | Avery |
| 4,608,985 A | 9/1986 | Crish et al. |
| 4,649,936 A | 3/1987 | Ungar et al. |
| 4,803,988 A | 2/1989 | Thomson |
| 4,813,418 A | 3/1989 | Harris |
| 5,702,429 A | 12/1997 | King |
| 5,925,070 A | 7/1999 | King et al. |
| 5,948,007 A | 9/1999 | Starkebaum et al. |
| 6,083,252 A | 7/2000 | King et al. |
| 6,152,882 A | 11/2000 | Prutchi |
| 6,505,078 B1 | 1/2003 | King et al. |
| 6,516,227 B1 | 2/2003 | Meadows et al. |
| 6,600,954 B2 | 7/2003 | Cohen et al. |
| 6,892,098 B2 | 5/2005 | Ayal et al. |
| 6,907,295 B2 | 6/2005 | Gross et al. |
| 6,928,320 B2 | 8/2005 | King |
| 2003/0045914 A1 | 3/2003 | Cohen et al. |
| 2003/0139781 A1 | 7/2003 | Bradley et al. |
| 2004/0127953 A1 | 7/2004 | Kilgore et al. |
| 2004/0162594 A1 | 8/2004 | King |
| 2005/0149148 A1 | 7/2005 | King |
| 2005/0149154 A1 | 7/2005 | Cohen et al. |

*Primary Examiner* — Allen Porter, Jr.
(74) *Attorney, Agent, or Firm* — Faegre Baker Daniels LLP

(57) ABSTRACT

Apparatus and methods for stimulating tissue employing local current imbalance to facilitate more effective stimulation regimens.

12 Claims, 9 Drawing Sheets

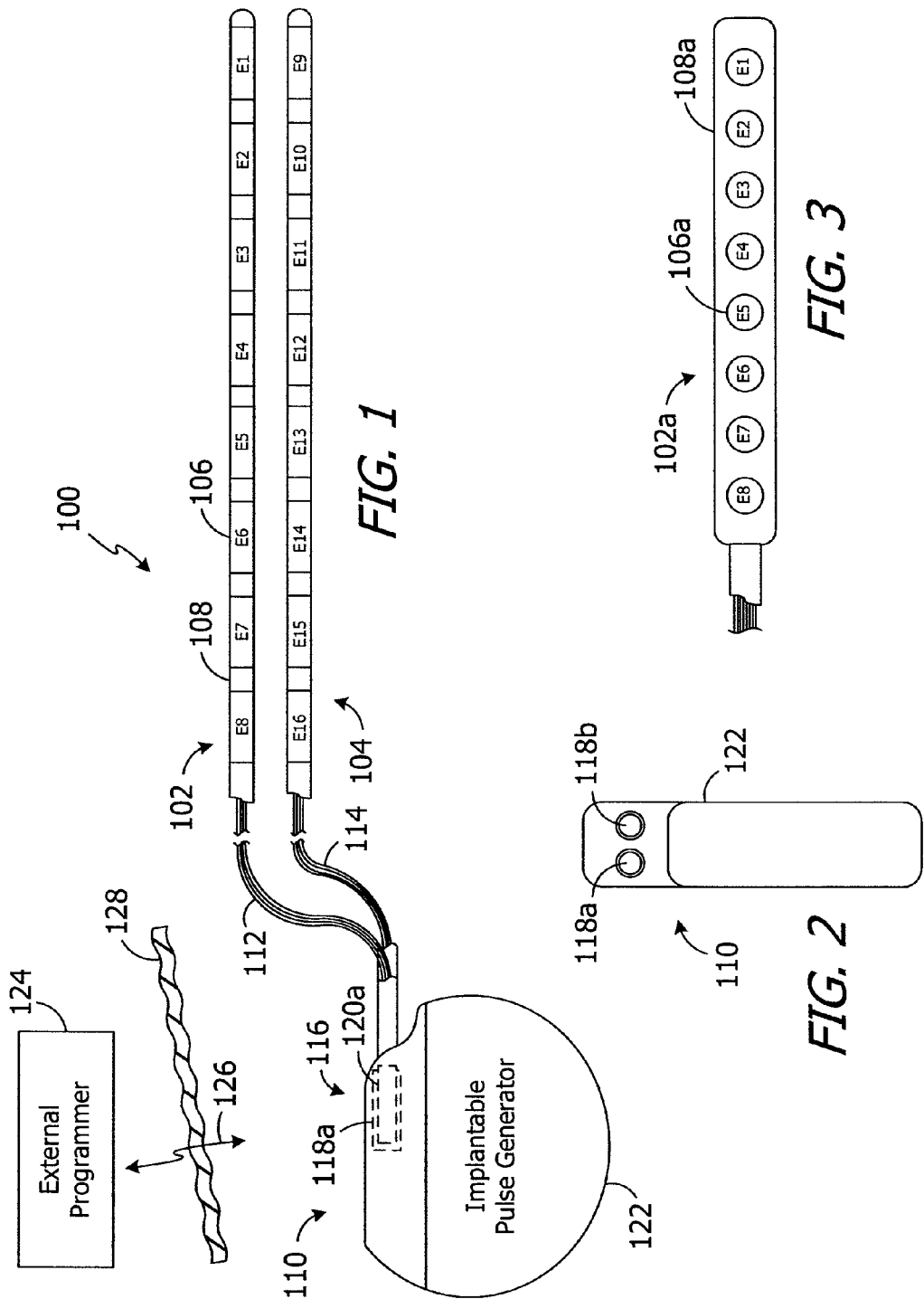

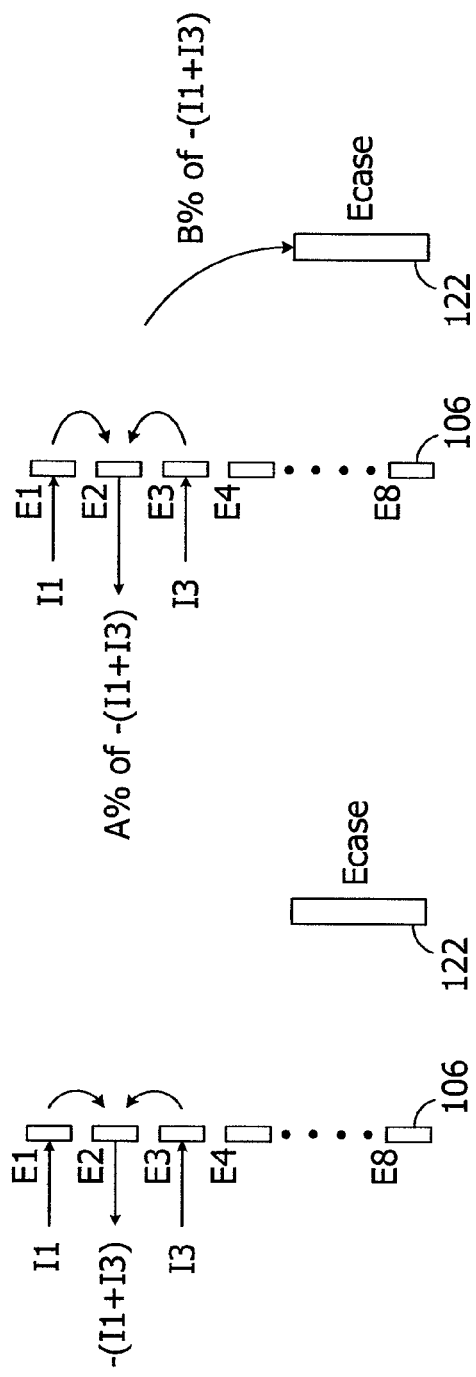
FIG. 5
FIG. 6
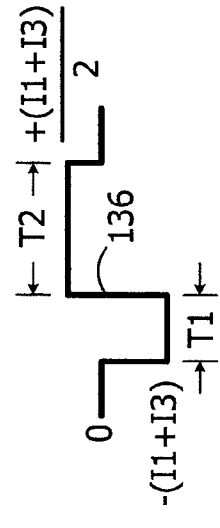
FIG. 7
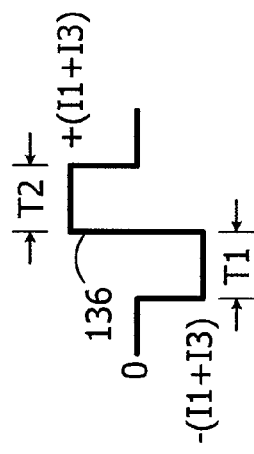
FIG. 8

APPARATUS AND METHODS FOR STIMULATING TISSUE

RELATED APPLICATION

The present application is a continuation of U.S. patent application Ser. No. 12/173,169, filed Jul. 15, 2008, which is a continuation of U.S. patent application Ser. No. 11/300,963, filed Dec. 15, 2005. The foregoing applications are each hereby incorporated by reference into the present application in their entirety.

BACKGROUND OF THE INVENTIONS

1. Field of Inventions

The present inventions relate generally to neurostimulation systems.

2. Description of the Related Art

Neurostimulation systems, such as spinal cord stimulation (SCS) systems, deep brain stimulation systems and peripheral nerve stimulation systems, include at least one electrode positioned to enable stimulation of neural elements that are the target tissue (i.e. the tissue that, when sufficiently stimulated, will create the desired therapeutic effect). The electrodes are commonly mounted on a carrier and, in many instances, a plurality of electrodes are mounted on a single carrier. These carrier/electrode devices are sometimes referred to as "leads." The electrodes may be used to cause nerves to fire action potentials (APs) that propagate along the neural fibers. More specifically, supplying stimulation energy to an electrode functioning as a cathode creates an electric potential field that causes depolarization of the neurons adjacent to the electrode. When the field is strong enough to depolarize (or "stimulate") the neurons beyond a threshold level, the neurons will fire APs.

Stimulation energy may be delivered to the electrodes during and after the lead placement process in order to verify that the electrodes are stimulating the target neural elements and to formulate the most effective stimulation regimen. The regimen will dictate which of the electrodes are sourcing or returning current pulses at any given time, as well as the magnitude and duration of the current pulses. The stimulation regimen will typically be one that provides stimulation energy to all of the target tissue that must be stimulated in order to provide the therapeutic benefit (e.g., pain relief), yet minimizes the volume of non-target tissue that is stimulated. Thus, certain types of neurostimulation leads are typically implanted with the understanding that the stimulus pattern will require fewer than all of the electrodes on the leads to achieve the desired clinical effect; in the case of SCS, such a clinical effect is "paresthesia," i.e., a tingling sensation that is effected by the electrical stimuli applied through the electrodes.

The present inventor has determined that conventional stimulus regimens, and the manner in which they are formulated, may be susceptible to improvement. For example, there are instances where the target tissue is not directly adjacent to an electrode and, because electrical field strength decreases exponentially with distance from the electrode, a relatively strong electric field must be created to generate APs in the target neural fibers. The electric field may, however, result in the generation of APs in the non-target fiber bundles between the electrode and the target fibers. The generation of APs in the non-target tissue may, in turn, lead to undesirable outcomes (e.g., discomfort) for the patient. The present inventor has determined that it may also be desirable in, for example, the context of leads that are oriented transverse to the target neural fibers, to selectively control the shape of the AP generating region in order to prevent the generation of APs in non-target fibers.

SUMMARY OF THE INVENTIONS

Apparatus and methods in accordance with some of the present inventions involve the creation of APs in neural fibers and the selective blocking of the APs in some of the neural fibers in which APs are created. Such apparatus and methods are advantageous for a variety of reasons. For example, such apparatus and methods facilitate stimulation regimens that create APs in tissue that is not directly adjacent to the depolarizing electrode(s) while preventing APs from propagating in the tissue therebetween that produce undesirable outcomes for the patient.

Apparatus and methods in accordance with some of the present inventions involve the use of local current imbalances and the sinking of current at a remote cathode(s). Such apparatus and methods are advantageous for a variety of reasons including, but not limited to, facilitation of the selective control of the width and depth of AP generating regions. For example, the programmer may increase the current sourced at one or more electrodes within the stimulation site, which tends to reduce the width of the AP generating and propagating region, without a corresponding increase in the current sunk at one or more other electrodes within the stimulation site (which would increase the depth of the AP generating region).

The above described and many other features of the present inventions will become apparent as the inventions become better understood by reference to the following detailed description when considered in conjunction with the accompanying drawings.

BRIEF DESCRIPTION OF THE DRAWINGS

Detailed description of exemplary embodiments of the inventions will be made with reference to the accompanying drawings.

FIG. 1 is a side view of a neurostimulation system in accordance with one embodiment of a present invention.

FIG. 2 is an end view of an implantable pulse generator in accordance with one embodiment of a present invention.

FIG. 3 is a plan view of a lead in accordance with one embodiment of a present invention.

FIG. 5 is a diagram showing a stimulation regimen that may be produced by the implantable pulse generator illustrated in FIG. 1.

FIG. 6 is a diagram showing another stimulation regimen that may be produced by the implantable pulse generator illustrated in FIG. 1.

FIG. 7 is an illustration of a stimulation pulse that may be produced by the implantable pulse generator illustrated in FIG. 1.

FIG. 8 is an illustration of another stimulation pulse that may be produced by the implantable pulse generator illustrated in FIG. 1.

DETAILED DESCRIPTION OF THE EXEMPLARY EMBODIMENTS

Figure 4:
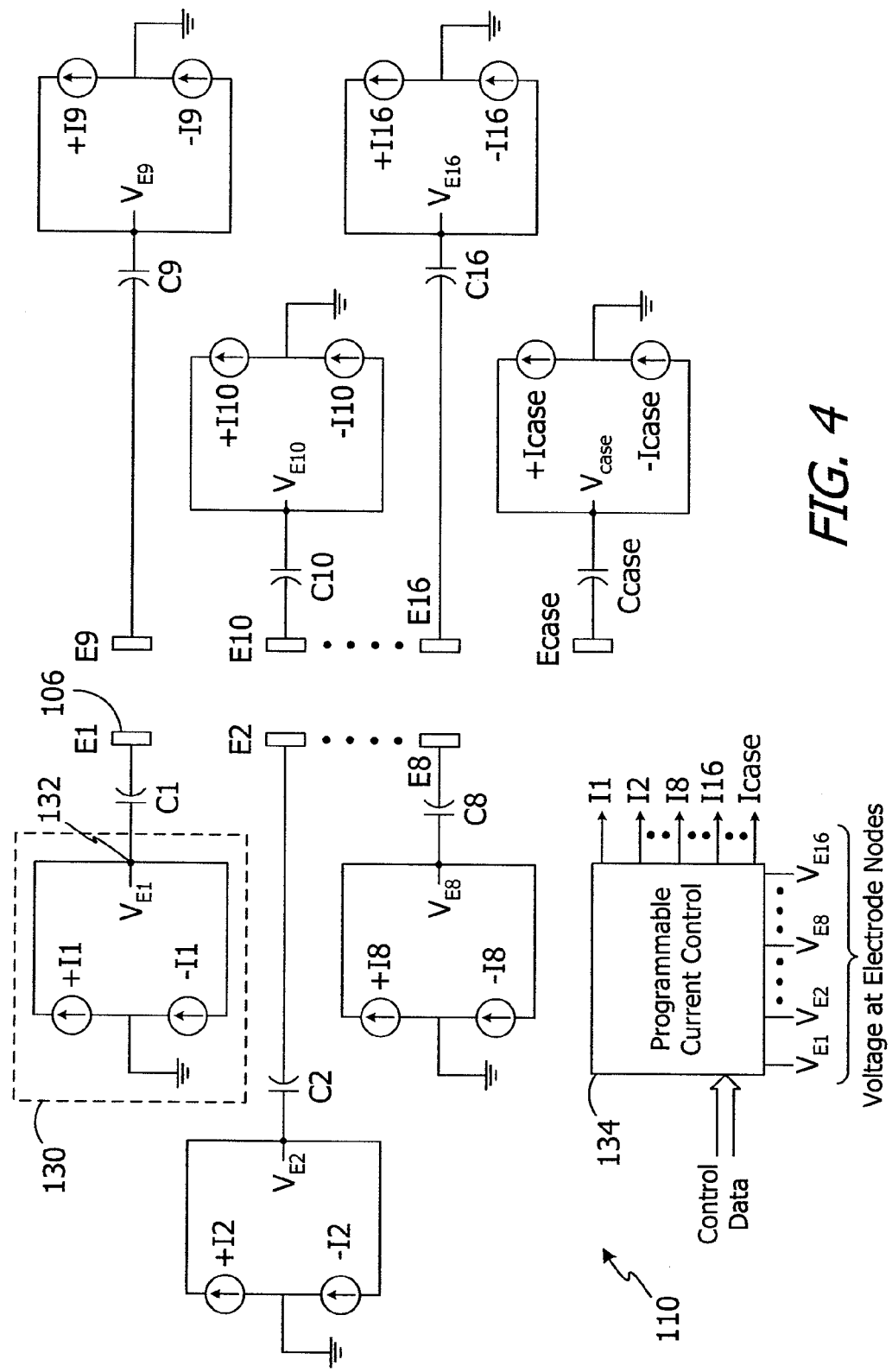
FIG. 4 is a functional block diagram of an implantable pulse generator in accordance with one embodiment of a present invention.

The following is a detailed description of the best presently known modes of carrying out the inventions. This description is not to be taken in a limiting sense, but is made merely for the purpose of illustrating the general principles of the inventions. The detailed description is organized as follows:

I. Exemplary Neurostimulation Systems
II. Exemplary Neurostimulation Regimens

The section titles and overall organization of the present detailed description are for the purpose of convenience only and are not intended to limit the present inventions.

I. Exemplary Neurostimulation Systems

The present inventions have application in a wide variety of neurostimulation systems. Although the present inventions are not so limited, examples of such systems are illustrated in FIGS. 1-9. Referring first to FIGS. 1 and 2, an exemplary implantable neurostimulation system 100 includes first and second implantable leads 102 and 104. The exemplary leads 102 and 104 are in-line leads and, to that end, both of the leads consist of a plurality of in-line electrodes 106 carried on a flexible body 108. In the illustrated embodiment, there are eight (8) electrodes on lead 102, which are labeled E1-E8, and there are eight (8) electrodes on lead 104, which are labeled E9-E16. The actual number of leads and electrodes will, of course, vary according to the intended application and the present inventions are not limited to any particular numbers of leads and electrodes. The implantable neurostimulation system 100 may, alternatively, employ other types of leads such as, for example, the paddle lead 102a with electrodes 106a on a wide platform 108a illustrated in FIG. 3. In any case, the leads may be implanted into a desired location, such as adjacent to the patient's spinal cord, through the use of an insertion needle or other conventional techniques. Once in place, the electrodes may be used to supply stimulation energy to the target neural elements or other target tissue.

The exemplary neurostimulation system 100 illustrated in FIGS. 1 and 2 also includes an implantable pulse generator (IPG) 110 that is capable of directing stimulation energy to each of the electrodes 106. The stimulation energy may be stimulation energy waveforms such as, for example, pulses having various shapes and sine waves. To that end, each of the electrodes 106 on the lead 102 is electrically connected to the IPG 110 by a respective signal wire 112 (some of which are not shown) that extends through, or is imbedded in, the associated flexible body 108. Similarly, the electrodes 106 on the lead 104 are electrically connected to the IPG 110 by respective signal wires 114 (some of which are not shown). The signal wires 112 and 114 are connected to the IPG 110 by way of an interface 116. The interface 116 may be any suitable device that allows the leads 102 and 104 to be removably or permanently electrically connected to the IPG 110. Such an interface may, for example, be an electro-mechanical connector arrangement including lead connectors 118a and 118b within the IPG 110 that are configured to mate with corresponding connectors on the leads 102 and 104 (only connector 120a on lead 102 is shown). Alternatively, the leads 102 and 104 can share a single connector that mates with a corresponding connector on the IPG. Exemplary connector arrangements are disclosed in U.S. Pat. Nos. 6,609,029 and 6,741,892, which are incorporated herein by reference.

The exemplary IPG 110 includes an outer case 122 that may be formed from an electrically conductive, biocompatible material such as titanium and, in some instances, will function as an electrode. The IPG 110 is typically programmed, or controlled, through the use of an external (non-implanted) programmer 124. The external programmer 124 is coupled to the IPG 110 through a suitable communications link, represented by the arrow 126, that passes through the patient's skin 128. Suitable links include, but are not limited to, radio frequency (RF) links, inductive links, optical links and magnetic links. The programmer 124 or other external device may also be used to couple power into the IPG 110 for the purpose of operating the IPG or replenishing a power source, such as a rechargeable battery, within the IPG. Once the IPG 110 has been programmed, and its power source has been charged or otherwise replenished, the IPG may function as programmed without the external programmer 124 being present.

With respect to the stimulus regimens provided during operation of the exemplary neurostimulation system 100, electrodes that are selected to receive stimulation energy are referred to herein as "activated," while electrodes that are not selected to receive stimulation energy are referred to herein as "non-activated." Electrical stimulation will occur between two (or more) electrodes, one of which may be the IPG case, so that the electrical current associated with the stimulus has a path through the tissue from one or more electrodes configured as anodes to one or more electrodes configured as cathodes, or return electrodes. The return electrode(s) may be one or more of the electrodes 106 on the leads 102 and 104 or may be the IPG case 122. Stimulation energy may be transmitted to the tissue in monopolar, bipolar, or multipolar fashion, as examples. Monopolar stimulation occurs when a selected one of the lead electrodes 106 is activated along with the case 122. Bipolar stimulation occurs when two of the lead electrodes 106 are activated. The lead electrodes 106 may be on the same lead, or on different leads. For example, electrode E3 on lead 102 may be activated as an anode at the same time that electrode E4 on lead 102, or electrode E11 on lead 104, is activated as a cathode. Tripolar stimulation occurs when three of the lead electrodes 106 are activated on the same lead, or on different leads. For example, electrodes E4 and E6 on lead 102 may be activated as anodes at the same time that electrode E5 on lead 102, is activated as a cathode. Generally speaking, multipolar stimulation occurs when multiple lead electrodes 106 are activated.

Turning to FIG. 4, an exemplary IPG 110 has a plurality of dual current sources 130. Each dual current source 130 includes a positive current source that can function as an anode (+I1, +I2, +I3, . . . +Icase) to "source" current to a load, as well as a current source that can function as a cathode (−I1, −I2, −I3, . . . −Icase) to "sink" current from the load, through a common node 132. The load is the tissue that resides between the activated electrodes 106, the wires (and other conductive elements), and the coupling capacitor (C1, C2, C3, . . . Ccase) that connects the associated electrode to the common node 132 of the dual current source 130.

The IPG programming will dictate which of the electrodes, i.e. the lead electrodes 106 and the IPG case 122, will act as source(s) and sink(s) at any particular time. To that end, the IPG 110 is provided with a programmable current control circuit 134 that causes selected dual current sources 130 to operate as an anode or a cathode, at specified times, to source or sink current having predetermined amplitude (and other parameters). In the illustrated embodiment, where there are eight (8) electrodes 106 on lead 102 (labeled E1-E8), eight (8) electrodes on lead 104 (E9-E16), and an IPG case 122 that can function as an electrode (labeled Ecase), there are seventeen individually operable dual current sources 130. The control circuit 134, which typically operates in accordance with stored control data that is received from the programmer 124, also turns off the selected dual current sources 130 at specified times. Alternative implementations may, for instance, employ fewer dual current sources than there are electrodes. Here, at least some of the dual current sources will be connected to more than one electrode. Alternative implementations may also be configured such that the IPG case 122 only functions as an anode, or such that the IPG case only functions as a cathode The operation of the control circuit 134 may be explained in the context of the following example. Referring to FIG. 5, the control circuit 134 may be used to simultaneously turn on (or enable) the positive current sources in the dual current sources 130 connected to lead electrodes E1 and E3 during time T1. The negative current source in the dual current source 130 connected to lead electrode E2 is also turned on during time T1. All other current sources are off (or disabled) during the time T1. This causes electrodes E1 and E3 to be activated as anodes at the same time that electrode E2 is activated as a cathode. Currents +I1 and +I3 are sourced from electrodes E1 and E3 at the same time that current −I2 is sunk into electrode E2. The amplitudes of the currents +I1 and +I3 may be any programmed values, and the amplitude of the current −I2 will be equal to −(I1+I3). That is, the current that is sourced from electrodes E1 and E3 is equal to the current that is sunk at electrode E2. Sinking all of the current sourced into the target tissue region at the target tissue region is referred to herein as "local current balance." As used herein, "local" electrodes are electrodes that, when sourcing or sinking stimulation current in the vicinity of the target tissue, have a clinically significant neuromodulatory effect on the target tissue.

As another example, the control circuit 134 may be used to cause a portion of the current sourced from one or more lead electrodes to be sunk by one (or more) lead electrodes and the remainder of the current to be sunk at the IPG case. Turning to FIG. 6, and for reasons that are discussed in greater detail below with reference to FIGS. 12, 13, 15 and 16, the control circuit 134 may be used to simultaneously turn on (or enable) the positive current sources in the dual current sources 130 connected to lead electrodes E1 and E3 during time T1. The negative current sources in the dual current source 130 connected to lead electrode E2 and case electrode Ecase are also turned on during time T1. All other current sources are off (or disabled) during the time T1. This causes electrodes E1 and E3 to be activated as anodes at the same time that electrodes E2 and Ecase are activated as cathodes. Currents +I1 and +I3 are sourced from electrodes E1 and E3 at the same time that current −I2 and −Icase is sunk into electrodes E2 and Ecase.

The amplitudes of the currents +I1 and +I3 may be any programmed values, while the sum of the amplitudes of the currents −I2 and −Icase will be equal to −(I1+I3), i.e., −I2 will be equal to A % of −(I1+I3) and −Icase will be equal to B % of −(I1+I3), where A %+B %=100%. That is, the sum of the current that is sourced from electrodes E1 and E3 is equal to the sum of the current that is sunk at electrodes E2 and Ecase. Sinking a portion of the current sourced into the target tissue region at a remote location, such as at the case electrode Ecase, is referred to herein as "local current imbalance." As used herein, a "remote" electrode is an electrode that, when sourcing or sinking stimulation current, will not have a clinically significant neuromodulatory effect on the target tissue other than reducing the amount of current sourced or sunk at the target tissue.

After time period T1, the control circuit 134 will typically switch the polarities of the electrodes during a second time period T2. Thus, an electrode that was functioning as an anode during time period T1 will function as a cathode during time period T2, and an electrode that was functioning as a cathode during time period T1 will function as an anode during time period T2. Operating the control circuit 134 in this manner produces a biphasic stimulation pulse that is characterized by a first phase (period T1) of one polarity followed by a second phase immediately or shortly thereafter (period T2) of the opposite polarity. The electrical charge associated with the first phase should be equal to the charge associated with the second phase to maintain charge balance during the stimulation, which is generally considered an important component of stimulation regimes, although this is not required by the present inventions. Referring to FIG. 7, the charge balance of a biphasic stimulation pulse 136 may be achieved by making the amplitudes of the first and second phases, as well as the periods T1 and T2, substantially equal. Charge balance may also be achieved using other combinations of phase duration and amplitude. For example, the amplitude of the second phase may be equal to one-half of the amplitude of the first phase and the period T2 may be equal to twice the period T1, as is the case in the biphasic stimulation pulse 136' illustrated in FIG. 8.

Figure 9:
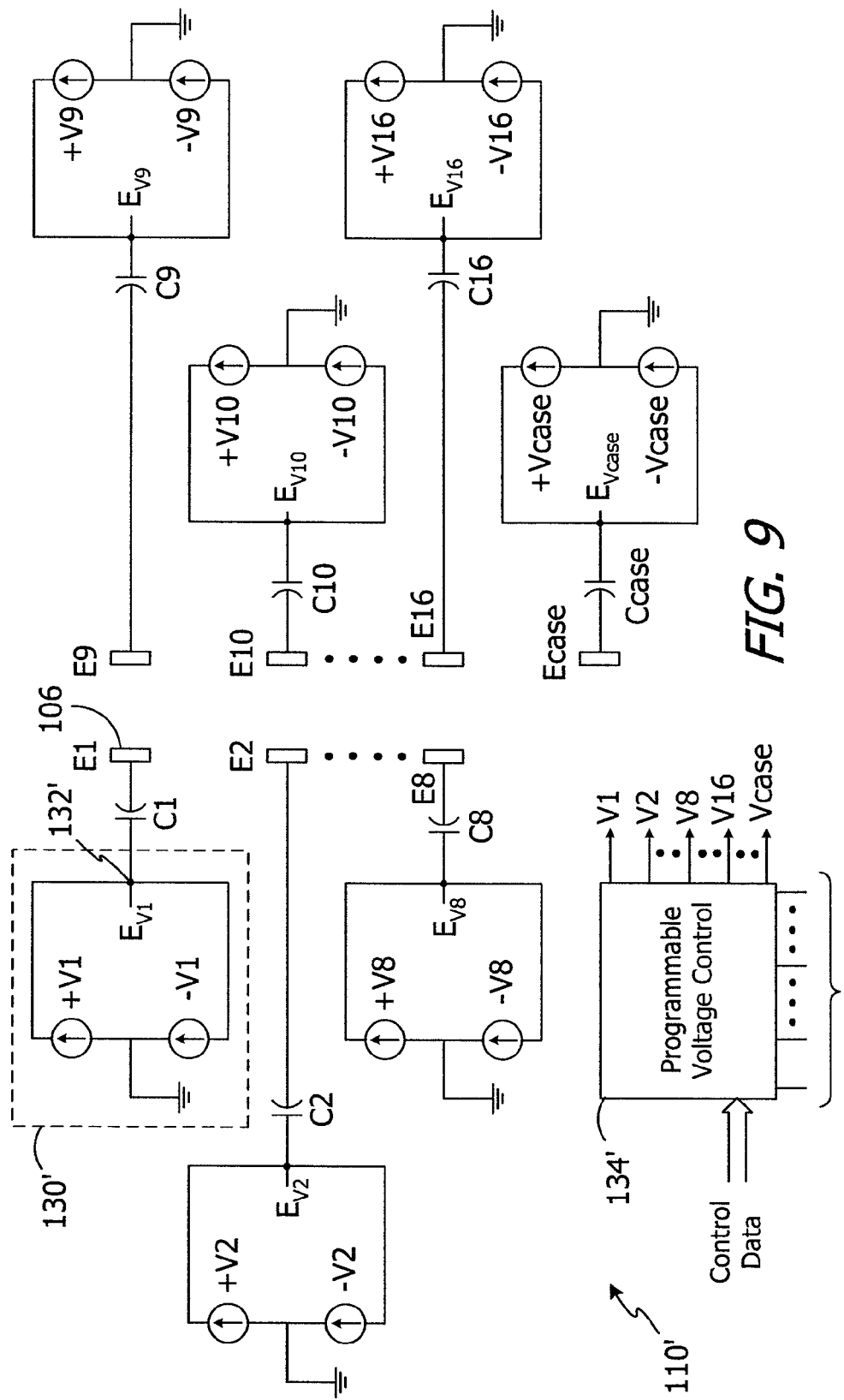
FIG. 9 is a functional block diagram of an implantable pulse generator in accordance with one embodiment of a present invention.

Neurostimulation systems in accordance with the present inventions may also employ the alternative IPG 110' illustrated in FIG. 9, which includes a plurality of dual voltage sources 130' that are respectively connected to the lead electrodes E1-E16 and the IPG case electrode Ecase. Each dual voltage source 130' applies a programmed voltage to the associated electrode when turned on by way of a node 132' and a coupling capacitor (C1, C2, C3, . . . Ccase). Alternative implementations may, as an example, employ fewer dual voltage sources than there are electrodes. Here, at least some of the dual voltage sources will be connected to more than one electrode. A programmable voltage control circuit 134' controls each of the dual voltage sources 130' and specifies the amplitude, polarity and duration of the voltage that is applied to the electrodes.

The dual voltage sources 130' and control circuit 134' may be used to produce the biphasic stimulation pulses that are characterized by a first phase (period T1) of one polarity followed by a second phase immediately or shortly thereafter (period T2) of the opposite polarity applied between any two or more electrodes. Charge balance of the biphasic stimulation pulse may be achieved by making the amplitudes of the first and second phases, as well as the periods T1 and T2, equal. Charge balance may also be achieved using other combinations of phase duration and amplitude. For example, the amplitude of the second phase may be equal to one-half of the amplitude of the first phase and the period T2 may be equal to twice the period T1.

Additional details concerning IPGs may be found in U.S. Pat. No. 6,516,227 and U.S. Pub. App. 2003/0139781, which are incorporated herein by reference. It also should be noted that the block diagrams illustrated in FIGS. 4 and 9 are functional diagrams, and are not intended to limit the present inventions to any particular IPG circuitry.

The present inventions also have application in non-implantable neurostimulation systems. For example, the present inventions may be embodied in, and/or performed using, transcutaneous electrical nerve stimulation ("TENS") systems. In TENS systems, the sourcing and sinking electrodes are placed on the patient's skin. Current is sourced into the neural tissue by way of the skin. Current is also sunk, both locally and remotely, by way of the skin.

II. Exemplary Neurostimulation Regimens

Figure 14:
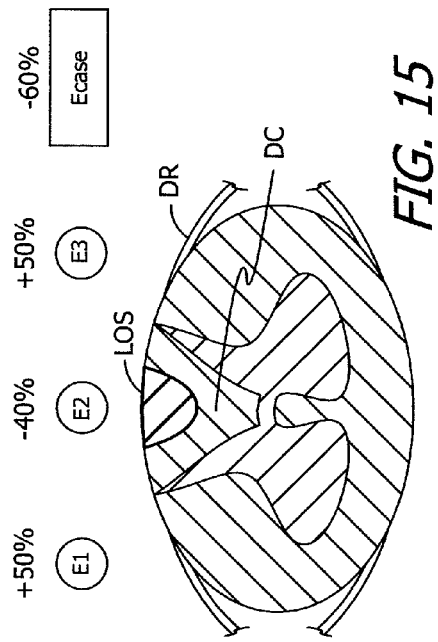
FIG. 14 is a section view of a dorsal column being treated with a conventional neurostimulation regimen.
Figure 15:
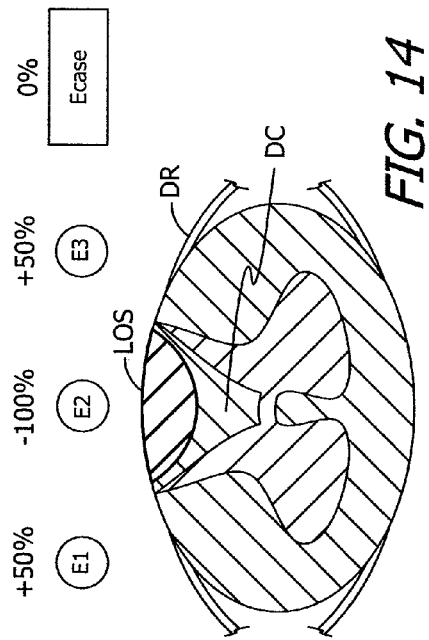
FIG. 15 is a section view of a dorsal column being treated with a neurostimulation regimen in accordance with one embodiment of a present invention.
Figure 16:
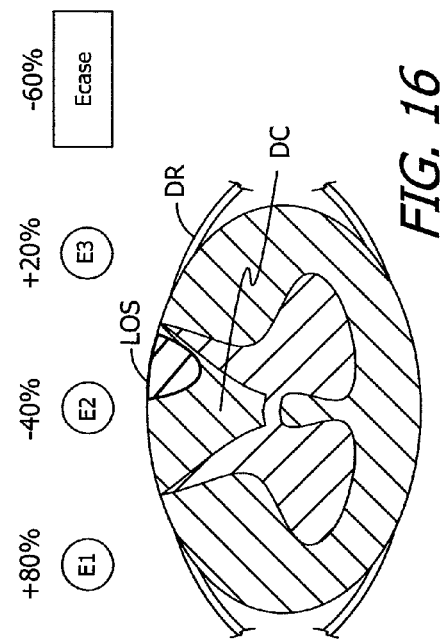
FIG. 16 is a section view of a dorsal column being treated with a neurostimulation regimen in accordance with one embodiment of a present invention.

The neurostimulation systems described above with reference to FIGS. 1-9 have application in a wide variety of stimulation regimens. Examples of such regimens are illustrated in FIGS. 10-16. FIGS. 10-13 graphically illustrate the changes in transmembrane potential ($\Delta Vm$) of neural fibers in fiber bundles that are in the vicinity of certain electrodes when electric fields are generated by the electrodes during the neurostimulation regimens, while FIGS. 14-16 highlight portions of tissue structures where the change in transmembrane potential is above a predetermined level. The neurostimulation regimens illustrated in FIGS. 10-13 are associated with neurostimulation systems employing a lead that is generally parallel to the neural fibers, while the neurostimulation regimens illustrated in FIGS. 14-16 are associated with neurostimulation systems employing a lead that is generally transverse to the neural fibers. Additionally, although the present inventions are not so limited, the regimens illustrated in FIGS. 10-13 are discussed in the context of first and second fiber bundles FB1 and FB2. In the illustrated examples, the first fiber bundle FB1 is the closest fiber bundle to the electrodes, the second fiber bundle FB2 is the next closest fiber bundle to the electrodes, and the first fiber bundle is located between the second fiber bundle and the electrodes.

Figures 10, 11:
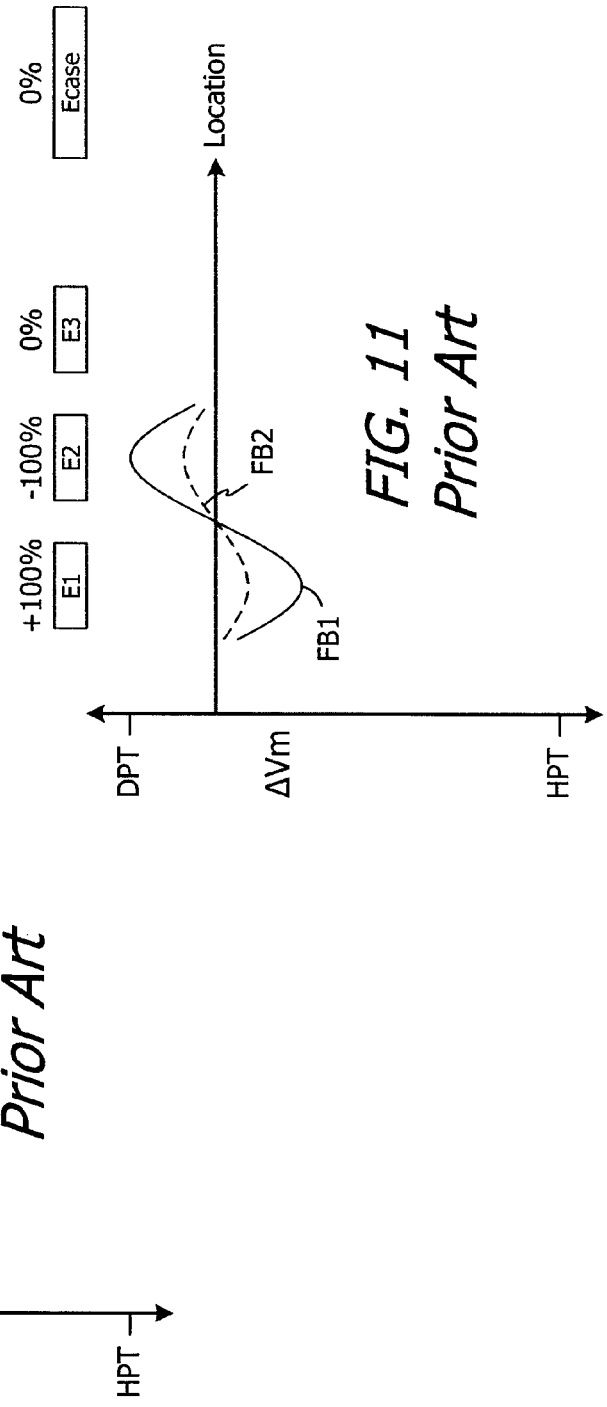
FIG. 10 is a graph of the changes in neural fiber transmembrane potential that results from a conventional neurostimulation regimen.
FIG. 11 is a graph of the changes in neural fiber transmembrane potential that results from another conventional neurostimulation regimen.

Conventional stimulation regimens for use with a lead that is generally parallel to the neural fibers, which serve as a reference for certain stimulation regimens in accordance with the present inventions, are illustrated in FIGS. 10 and 11. In FIG. 10, electrodes E1-E3 are activated in a conventional stimulation regimen where electrodes E1 and E3 are functioning as anodes and electrode E2 is functioning as a cathode. No current is sourced or sunk at any of the other electrodes. Electrodes E1 and E3 are each sourcing 50% of the total current (e.g., 1 mA each) and 100% of the total current (e.g., 2 mA) is being sunk at electrode E2. As such, there is local current balance at the stimulation site. The depolarizing electric field generated by electrode E2 is sufficient to create APs in some of the neural fibers in the first fiber bundle FB1. In other words, the depolarization threshold DPT has been met for the first fiber bundle FB1 in the tissue adjacent electrode E2. The depolarizing electric field generated by electrode E2 is substantially weaker at the second fiber bundle FB2 and is below the AP-creating depolarization threshold DPT. The locus of stimulation is, therefore, defined by the portion of the depolarizing electric field generated by electrode E2 that is at or above the depolarization threshold DPT.

Electrodes E1 and E3, which are functioning as anodes in the stimulation regimen illustrated in FIG. 10, will create hyperpolarizing electric fields in the neural tissue adjacent to electrodes E1 and E3. When the electric field is at or above the hyperpolarization threshold HPT, the neural fibers within the electric field will block APs that were fired at other points along the fibers. It should be noted here that the magnitude of the hyperpolarization threshold HPT has been estimated to be about 2 to 8 times the magnitude of the depolarization threshold DPT. The hyperpolarizing electric fields generated by electrodes E1 and E3 in the exemplary stimulation regimen are below the hyperpolarization threshold HPT at the first fiber bundle FB1. As such, APs in the fiber bundle FB1 that fired at points in the neural fibers adjacent to electrode E2 will not be blocked at points adjacent to electrodes E1 and E3. The hyperpolarizing electric fields generated by electrodes E1 and E3 will, of course, be even weaker at the second fiber bundle FB2.

Turning to FIG. 11, electrodes E1 and E2 are activated in a conventional stimulation regimen where electrode E1 is functioning as an anode and electrode E2 is functioning as a cathode. No current is sourced at any other electrode. All of the current sourced at electrode E1 (e.g. 2 mA) is being sunk at electrode E2 and there is local current balance. With respect to the first fiber bundle FB1, the depolarizing electric field generated by electrode E2 meets the depolarization threshold DPT, which will result in the generation of APs by at least some of the fibers in the first fiber bundle. The hyperpolarizing electric field generated by electrode E1 is below the hyperpolarization threshold HPT and, accordingly, the APs will not be blocked. Within the fiber bundle FB2, the depolarizing electric field generated by electrode E2 is below the depolarization threshold DPT and the hyperpolarizing electric field generated by electrode E1 is below the hyperpolarization threshold HPT.

In both of the regimens described above, the generation of APs in the fibers within the second fiber bundle FB2 will require an increase in the depolarizing electric field generated by electrode E2 over that illustrated in FIGS. 10 and 11. There may be instances where the generation of APs in the first fiber bundle FB1, which necessarily results from the creation of a depolarizing electric field that is strong enough to meet the depolarization threshold DPT at the second fiber bundle FB2, may lead to undesirable outcomes (e.g. discomfort or undesirable reflexive activity) for the patient. Some of the present inventions solve this problem by preventing APs generated in the first fiber bundle FB1 from reaching the brain or end organ. Specifically, such inventions create local AP blocks and the AP blocks prevent APs created within a portion of the depolarizing electric field that is at or above the depolarization threshold DPT from traveling, in one direction or both directions, beyond the stimulation site. The effective locus of stimulation is, therefore, the region of neural fibers that are generating APs that are not blocked at other portions of the stimulation site.

Figure 12:
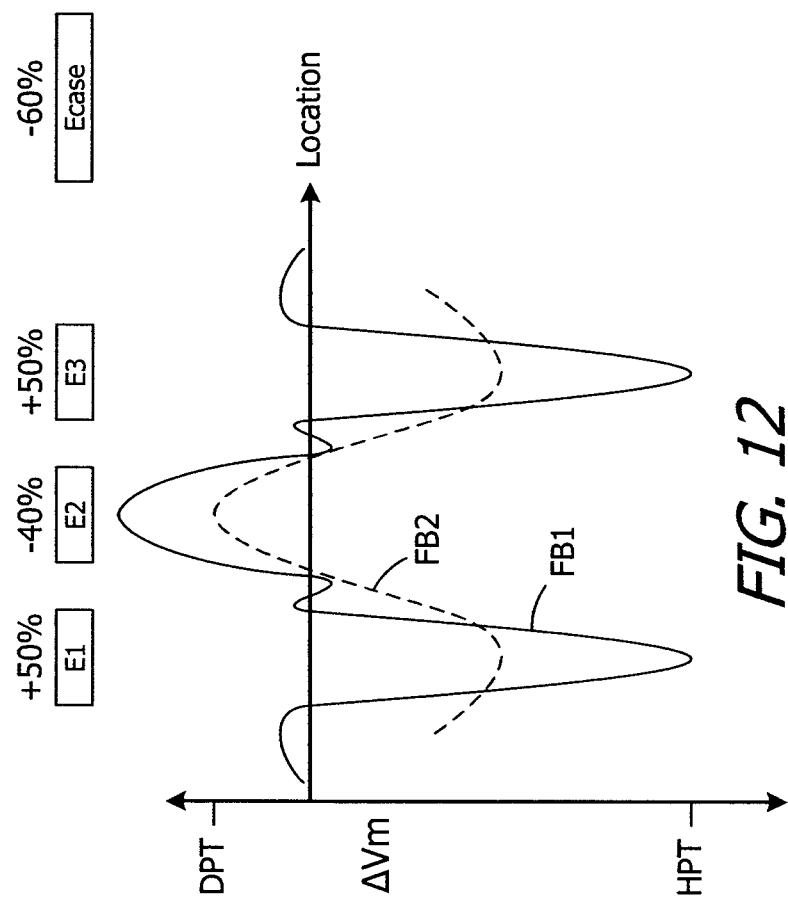
FIG. 12 is a graph of the changes in neural fiber transmembrane potential that results from a neurostimulation regimen in accordance with one embodiment of a present invention.

As illustrated in FIG. 12, one example of a stimulation regimen in accordance with a present invention involves locally blocking APs generated in the first fiber bundle FB1. At least a substantial portion of the APs (i.e., >10-20%) are blocked by hyperpolarizing tissue in the first fiber bundle FB1, located on opposite sides of the tissue in the first fiber bundle FB1 that is generating the APs, to at least the hyperpolarization threshold HPT. This may be accomplished by significantly increasing the level of current sourced from electrodes E1 and E3, as compared to the level illustrated in FIG. 10 (e.g., about 2.5 mA each), in order to reach the hyperpolarization threshold HPT within the first fiber bundle FB1 at electrodes E1 and E3. Turning to electrode E2, the amount of current sunk at electrode E2 should be sufficient to create a depolarizing electric field that is strong enough to meet the depolarization threshold DPT at the second fiber bundle FB2 and cause fibers within the second fiber bundle to generate APs.

The inventor herein has determined that sinking all of the current sourced by electrodes E1 and E3 at electrode E2 could result in a depolarizing electric field that would meet or exceed the depolarization threshold DPT in fiber bundles well beyond the second fiber bundle FB2. In those instances where the creation of APs beyond the second fiber bundle FB2 is undesirable, a portion of the current sourced by the electrodes E1 and E3 will be sunk at an electrode that is located remotely from stimulation site, thereby creating a local current imbalance at the stimulation site. Sinking some of the current at a remote electrode allows the intensity of the depolarizing electric field created by electrode E2 to be reduced to a level where the hyperpolarization threshold HPT will not be met in fibers within the second fiber bundle FB2.

The portion of the current in the exemplary stimulation regimen illustrated in FIG. 12 that is sourced by electrodes E1 and E3, but is not sunk at electrode E2, is sunk at the IPG case electrode Ecase. Although the relative amounts may vary to suit particular situations, a majority of the current is sunk at electrode Ecase in the illustrated example. More specifically, 60% of the current sourced by electrodes E1 and E3 is sunk at electrode Ecase and the remaining 40% is sunk at electrode E2. There are a variety of advantages associated with the use of the case electrode Ecase as a remote cathode in a locally imbalanced stimulation regimen. For example, because the case electrode Ecase will typically be much larger than the lead electrodes, the current density and electric field intensity will be greatly reduced. This reduces the likelihood that the non-target tissue in the vicinity of the case electrode Ecase will be stimulated. IPG cases are also electrode Ecase. Although the relative amounts may vary to suit particular situations, a majority of the current is sunk at E2 in the illustrated example. More specifically, 60% of the current sourced by electrode E1 is sunk at electrode E2 and the remaining 40% is sunk at electrode Ecase.

Turning to stimulation regimens for use with a lead that is oriented generally transverse to the neural fibers, and as illustrated for example in FIG. 14, such regimens frequently include electrodes over the center of the dorsal column DC and over the dorsal roots DR on either side of the dorsal column. A conventional stimulation regimen, which will serve as a reference for certain stimulation regimens in accordance with the present inventions, is illustrated in FIG. 14. Here, electrodes E1 and E3 are functioning as anodes and electrode E2 is functioning as a cathode. Electrodes E1 and E3 are each sourcing 50% of the total current (e.g., 1 mA each) and 100% of the total current (e.g., 2 mA) is being sunk at electrode E2. No other electrodes are activated and there is local current balance at the stimulation site. The combination of the hyperpolarizing electric fields generated by electrodes E1 and E3 and the depolarizing electric field generated by electrode E2 results in an area within the dorsal column DC that is at or above the depolarization threshold. This area, which has an overall depth and width, is the locus of stimulation LOS.

The present inventor has determined that locally current balanced stimulation regimens, such as that illustrated in FIG. 14, do not allow the depth and width of the locus of stimulation LOS to be highly controllable using only total current sunk and sourced. For example, conventional, locally-current-balanced stimulations regimens would not allow the regimen programmer to reduce the width of the regimen illustrated in FIG. 14 without effecting the depth. Stimulation regimens in accordance with some of the present inventions, on the other hand, employ a local current imbalance that facilitates high fidelity control of the width and depth of the locus of stimulation LOS.

As illustrated in FIG. 15, a stimulation regimen in accordance with one example of a present invention employs a local current imbalance and a remote cathode to provide the desired locus of stimulation LOS. More specifically, as compared to the stimulation regimen illustrated in FIG. 14, the stimulation regimen illustrated in FIG. 15 creates a locus of stimulation LOS that has a smaller width and the same depth. The current sourced at electrodes E1 and E3 is increased (e.g., 4-8 mA each) in order to strengthen the hyperpolarizing electric fields created thereby. Strengthening of the hyperpolarizing electric fields created by electrodes E1 and E3 tends to result in a narrowing the locus of stimulation LOS because it weakens the lateral edges of the depolarizing electric field created by electrode E2. Additionally, the amount of current sunk at electrode E2 may be controlled such that the depth of the locus of stimulation LOS is the same as that illustrated in FIG. 14. More specifically, a portion of the total current sourced at electrodes E1 and E3 (e.g., 40%) is sunk at electrode E2, which is functioning as a local cathode to depolarize tissue, and the remainder of the total current sourced at electrodes E1 and E3 (e.g., 60%) is sunk at a remote electrode. In the illustrated example, the remote electrode is the case electrode Ecase. No current is sourced or sunk by other electrodes in this example.

Current steering techniques may also be employed with local current imbalances to further control the locus of stimulation LOS. Referring for example to FIG. 16, the current sourced the electrodes E1 and E3 in the illustrated stimulation regimen is not equal. Electrode E1 is sourcing 80% of the total anodic current (e.g., 8 mA) and electrode E3 is sourcing the other 20% of the total anodic current (e.g., 2 mA). The locus of stimulation LOS is, accordingly, "steered" toward to electrode E3. With respect to the local current imbalance that is employed to control the depth of the locus of stimulation LOS, a portion of the total current sourced at electrodes E1 and E3 (e.g., 40%) is sunk at electrode E2 and the remainder of the total current sourced at electrodes E1 and E3 (e.g., 60%) is sunk at a remote electrode. Here too, the remote electrode is the case electrode Ecase. No current is sourced or sunk by other electrodes in this example.

Stimulation regimens that involve the local current imbalances of the type described above with reference to FIGS. 12, 13, 15 and 16 may be developed by the programmer during and/or after the lead placement process. For example, typically located in areas, such as a subcutaneous pocket in the abdomen, where there is not a substantial amount of tissue that is susceptible to stimulation.

It should be noted here that there are a variety ways to remotely sink current. One example is, as discussed above, sinking current at the remotely located case electrode Ecase. Current may also be sunk, for example, at some or all of the electrodes on a remotely implanted lead. Another example is sinking current at a dedicated, and preferably spherical, remotely implanted electrode on the end of a lead.

Figure 13:
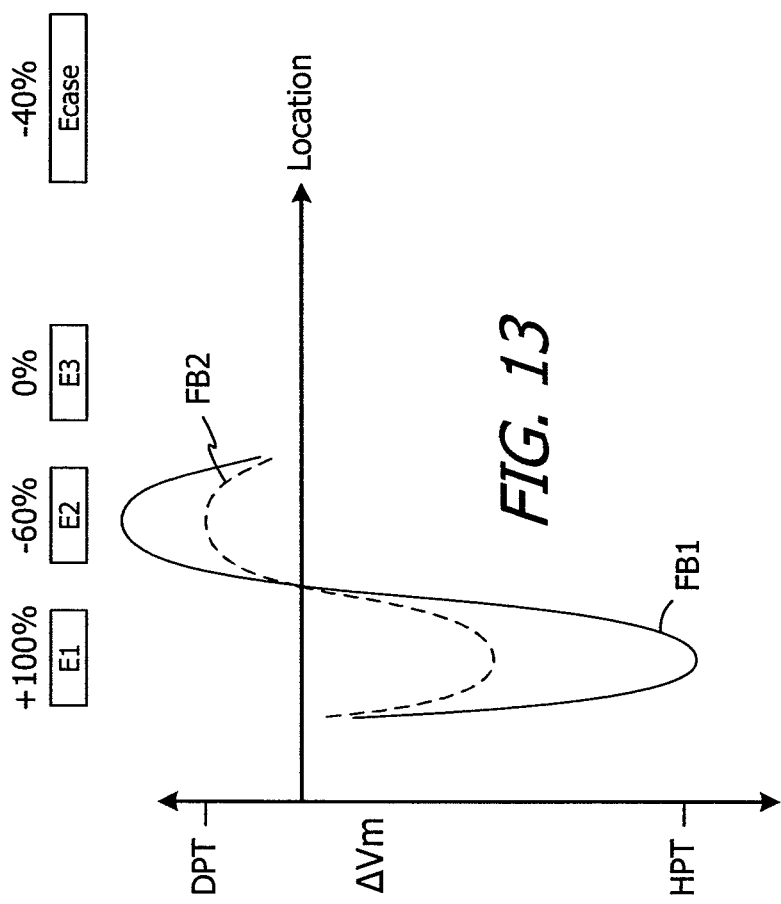
FIG. 13 is a graph of the changes in neural fiber transmembrane potential that results from a neurostimulation regimen in accordance with one embodiment of a present invention.

Another exemplary stimulation regimen in accordance with a present invention, which may be employed when AP block is only desired in a single direction, is illustrated in FIG. 13. Here, electrode E1 is functioning as an anode and electrode E2 is functioning as a cathode. No other local electrodes are sourcing or sinking current. The amount of current sourced from electrode E1 (e.g. about 4-8 mA) is sufficient to reach the hyperpolarization threshold HPT within the first fiber bundle FB1, thereby creating a local AP block at electrode E1 in at least a substantial portion of the fibers (i.e.

>10-20%) within the first fiber bundle. The amount of current being sunk at electrode E2 is sufficient to create a depolarizing electric field that is strong enough to meet the depolarization threshold DPT at the second fiber bundle FB2 and cause fibers within the second fiber bundle to generate APs. Such a depolarizing electric field will, of course, also cause the fibers in the first fiber bundle FB1 to generate APs. However, at least a substantial portion of the APs in the first fiber bundle FB1 will be prevented from passing electrode E1 by the hyperpolarization.

Figure 17:
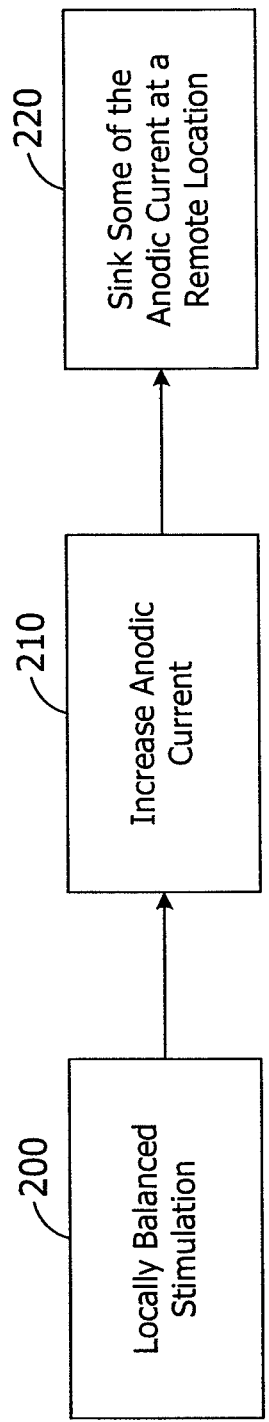
FIG. 17 is a flow chart summarizing various processes in accordance with the present inventions.

Additionally, in those instances where the creation of APs in fibers beyond the second fiber bundle FB2 is undesirable, a portion of the current sourced by electrode E1 will be sunk at an electrode that is located remotely from the stimulation site, thereby creating a local current imbalance at the stimulation site. As noted above, this reduces the intensity of the depolarizing electric field created by electrode E2 to a level where the hyperpolarization threshold HPT will not be met beyond the second fiber bundle FB2. In the illustrated regimen, the current from electrode E1 that is not sunk at electrode E2 is sunk at the IPG case and referring to FIG. 17, the external programmer 124 (FIG. 1) may be used to cause the IPG 110 to source and sink current in a locally balanced stimulation regimen of the type described above with reference to FIGS. 10, 11 and 14 after the lead(s) are in place (Step 200). In those instances where the stimulation regimen is not providing the desired paresthesia, the external programmer 124 may be used to cause the IPG 110 to increase the anodic current (Step 210). The additional anodic current may be used to block APs in certain fiber bundles (FIGS. 12 and 13) or to alter the shape of the portion of the electric field that is generating APs (FIGS. 15 and 16). If necessary, the external programmer 124 may also be used to cause the IPG 110 to create a locally imbalanced stimulation regimen, where some of the anodic current is sunk at a remote location such as the IPG case 122 (Step 220).

Although the inventions disclosed herein have been described in terms of the preferred embodiments above, numerous modifications and/or additions to the above-described preferred embodiments would be readily apparent to one skilled in the art. By way of example, but not limitation, the present inventions include neurostimulation systems that also comprise at least one neurostimulation lead. It is intended that the scope of the present inventions extend to all such modifications and/or additions and that the scope of the present inventions is limited solely by the claims set forth below.

I claim:

1. A method, comprising the steps of:
   selecting one or more electrodes in a vicinity of a target tissue to have a hyperpolarizing effect on a target tissue;
   selecting a first electrode being different from the one or more electrodes and being a local electrode in the vicinity of the target tissue, the first electrode adapted for sinking stimulation current to have a depolarizing effect on the target tissue;
   selecting a remote electrode being different from the one or more electrodes and being outside the vicinity of the target tissue, the remote electrode adapted for sinking stimulation current to reduce the amount of current sunk at the first electrode;
   sourcing current at the one or more electrodes at a magnitude sufficient to block at least some of the action potentials in a first neural fiber bundle contributing to an adverse side effect;
   sinking a first portion of current sourced from the one or more electrodes at the first electrode that is a first distance from the first neural fiber bundle and is a second distance from a second neural fiber bundle different from the first distance, wherein the first portion of the current sunk at the first electrode has a magnitude sufficient to generate action potentials in neural fibers in the first and second neural fiber bundles, wherein sinking the first portion of current creates a local charge imbalance in the vicinity of the target tissue; and
   sinking a second portion of the current sourced from the one or more electrodes at the remote electrode to sink stimulation current to reduce the amount of current sunk at the first electrode, and maintaining an overall charge balance among the one or more electrodes, the first electrode, and the remote electrode.

2. The method of claim 1, wherein the second distance is greater than the first distance.

3. The method of claim 1, wherein the remote electrode has a greater surface area than the first electrode.

4. The method of claim 1, wherein the first and second neural fiber bundles are located in a spinal cord.

5. The method of claim 1, wherein the magnitude of the second portion of the current is greater than the magnitude of the first portion of current.

6. The method of claim 1, wherein the one or more electrodes is the first distance from the first neural fiber bundle and the second distance from the second neural fiber bundle.

7. The method of claim 1, wherein the side-effect is one of discomfort and undesirable reflexive activity.

8. The method of claim 1, wherein blocking of the at least some of the action potentials in the first neural fiber bundle prevent the at least some of the action potentials from reaching a brain.

9. A method, comprising the steps of:
   sourcing current from one or more electrodes in a vicinity of a target tissue, wherein the one or more electrodes includes a second electrode and a third electrode;
   sinking a first portion of current sourced from one or more electrodes at a first electrode in the vicinity of the target tissue, the first electrode being a first distance from a first neural fiber bundle and being a second distance from a second neural fiber bundle different from the first distance, wherein the first portion of the current sunk at the first electrode has a magnitude sufficient to generate action potentials in neural fibers in the first and second neural fiber bundles, wherein the first electrode is between the second electrode and the third electrode and sinking the first portion of current creates a local charge imbalance in the vicinity of the target tissue;
   sinking a second portion of the current sourced from the one or more electrodes to a remote electrode outside the vicinity of the target tissue, wherein the current sourced by the one or more electrodes has a magnitude sufficient to block at least some of the action potentials in a first neural fiber bundle otherwise contributing to an adverse side effect, wherein the remote electrode is not between the second electrode and the third electrode; and
   maintaining a charge balance among the first electrode, the remote electrode, the second electrode, and the third electrode.

10. The method of claim 9, wherein the second electrode and third electrode are adjacent to the first electrode.

11. The method of claim 10, wherein the first and second nerve fiber bundles are located in a spinal cord, and wherein the first, second, and third electrodes are transversely arranged relative to the first and second nerve fiber bundles of the spinal cord.

12. A method, comprising the steps of:
sourcing current from one or more electrodes in a vicinity of a target tissue;
sinking a first portion of current sourced from the one or more electrodes at a first electrode in the vicinity of the target tissue, the first electrode being a first distance from a first neural fiber bundle and being a second distance from a second neural fiber bundle different from the first distance, wherein the first portion of the current sunk at the first electrode has a magnitude sufficient to generate action potentials in neural fibers in the first and second neural fiber bundles, wherein sinking the first portion of the current creates a local charge imbalance in the vicinity of the target tissue; and
sinking a second portion of the current sourced from the one or more electrodes to a remote electrode outside the vicinity of the target tissue, wherein the current sourced by the one or more electrodes has a magnitude sufficient to block at least some of the action potentials in the first neural fiber bundle otherwise contributing to an adverse side effect, wherein the remote electrode comprises a case of an implanted neurostimulator adapted for biphasic stimulation, and wherein sinking the second portion of current maintains a charge balance among the one or more electrodes, the first electrode, and the second electrode; and
switching the polarities of the one or more electrodes, the first electrode, and the remote electrode for another phase of biphasic stimulation.

* * * * *